United States Patent [19]
Tano et al.

[11] Patent Number: 5,300,063
[45] Date of Patent: Apr. 5, 1994

[54] OPHTHALMIC LASER APPARATUS

[75] Inventors: Yasuo Tano, Kobe; Masanori Enomoto, Nishio; Yasuo Ota, Gamagori, all of Japan

[73] Assignee: Nidek Co., Ltd., Gamagori, Japan

[21] Appl. No.: 879,386

[22] Filed: May 7, 1992

[30] Foreign Application Priority Data

May 11, 1991 [JP] Japan ................... 3-135548

[51] Int. Cl.[5] ............................................. A61B 17/32
[52] U.S. Cl. .......................................... 606/4; 606/15; 606/17
[58] Field of Search ............... 606/15, 16, 17, 4, 9, 606/10, 11, 12, 13; 385/31, 33, 39

[56] References Cited

U.S. PATENT DOCUMENTS

| | | | |
|---|---|---|---|
| 4,418,689 | 12/1983 | Kanazawa | 606/15 |
| 4,470,414 | 9/1984 | Imagawa et al. | |
| 4,672,969 | 6/1987 | Dew | 128/397 |
| 4,686,979 | 8/1987 | Gruen et al. | |
| 4,742,235 | 5/1988 | Koji | 250/504 |
| 4,793,679 | 12/1988 | Toda et al. | 385/39 |
| 4,849,859 | 7/1989 | Nagasawa | 606/16 |
| 4,860,743 | 8/1989 | Abela | 606/16 |
| 4,940,411 | 7/1990 | Vassiliadis et al. | 606/16 |
| 5,125,922 | 6/1992 | Dwyer et al. | 606/17 |
| 5,147,349 | 9/1992 | Johnson et al. | 606/17 |
| 5,151,097 | 9/1992 | Daikuzono | 606/17 |

Primary Examiner—Stephen C. Pellegrino
Assistant Examiner—Sonya Harris
Attorney, Agent, or Firm—Nikaido, Marmelstein, Murray & Oram

[57] ABSTRACT

An ophthalmic laser apparatus has a proper exit angle from a probe to prevent a sclera from being damaged when the probe is used to treat an eye of a patient. A laser beam emitted from a laser oscillator is directed to a light cable receptacle connector by an optical system. The laser beam is directed to a delivery optical system or a probe by a light cable having a connecting part at one end thereof to be connected to the light cable receptacle connector. The probe is bent near an end thereof and the end of the probe is generally spherically shaped.

9 Claims, 4 Drawing Sheets

OPHTHALMIC LASER APPARATUS

BACKGROUND OF THE INVENTION

The present invention relates to an ophthalmic laser apparatus, and more particularly to an ophthalmic laser apparatus suitable to a probe for transscleral retina photocoagulation.

A photocoagulation method in which a treatment light is directed to an ocular through an cornea from a lens system, and another photocoagulation method in which a treatment light is directed to an endprobe inserted into an eye through a light cable and the directed light is irradiated to an ocular, have been known as methods for photocoagulating the ocular of the eye to be treated. A treatment method in which a probe is inserted externally of the eye to be treated and the retina is photocoagulated by a YAG laser through the sclera, has also been known. Those treatment methods are selectively used depending on a position of the coagulation.

Since such an apparatus is expensive, it is usually not a stand-alone apparatus but it is shared with an apparatus for coagulating other than the ocular such as a ciliary body, and it is selectively used.

A cryocoagulation method in which a probe is inserted externally of the eye to be treated and the retina is coagulated through the sclera has also been known.

When the probe is to be inserted externally of the eye to be treated to photocoagulate the retina through the sclera, it is necessary to press the sclera in order to locate an affected part. Where a probe of a conventional shape is used, a tip end thereof is likely to damage the sclera.

Further, because the apparatus is not constructed as a stand-alone unit it is necessary to direct lights to a slit lamp, through a delivery optical system such as a binocular indirect ophthalmoscope, and various probes. As a result, there is a restriction in an incident angle to an optical fiber in the light cable for the probe and a divergence angle of a light beam at the end of the probe is not always optimum. When a semiconductor laser is used, the coagulation area per irradiation is ⅓ to 1/6 of the coagulation area attained by the cryocoagulation method and hence the number of times of irradiation increases.

There is a limit in controlling the spread angle in the laser apparatus.

SUMMARY OF THE INVENTION

It is a first object of the present invention to provide an ophthalmic laser apparatus which allows easy treatment of an eye without damaging a sclera even if a probe is inserted externally of the eye to be treated.

It is a second object of the present invention to provide an ophthalmic laser apparatus which can optimize a divergence angle at an end of the probe.

In order to achieve the above objects, the present invention is constructed as follows.

(1) An ophthalmic laser apparatus is provided for directing a laser beam to a delivery optical system or a probe by a light cable for directing the laser beam emitted from a laser oscillator to a light cable receptacle connector by an optical system and having a connecting part at one end thereof to be connected to the light cable receptacle connector, wherein probe is bent near an end thereof, and the end of the probe is generally spherical.

(2) An ophthalmic laser apparatus according to (1) probe is bent to deflect an exit direction by approximately 70–90 degrees.

(3) An ophthalmic laser apparatus according to (1) can also be configured such that the probe photocoagulates an ocular externally of an eye to be treated, through a sclera.

(4) An ophthalmic laser apparatus according to (1) can include a semiconductor laser oscillator as the laser oscillator.

(5) Another embodiment of the invention can include an ophthalmic laser apparatus for directing a laser beam to a delivery optical system or a probe by a light cable for directing the laser beam emitted from a laser oscillator to a light cable receptacle connector by an optical system and having a connecting part at one end thereof to be connected to the light cable receptacle connector, wherein an optical member for adjusting an exit divergence angle of the laser beam is arranged at the connecting part of the light cable connected to the probe.

(6) An ophthalmic laser apparatus according to (5) can be configured such that the optical member for adjusting the exit divergence angle is a convergence or divergence lens.

(7) An ophthalmic laser apparatus according to (5) can have the optical member for adjusting the exit divergence angle arranged at the connecting part of said light cable, and the end plane of the optical fiber in said light cable positioned at a combined focus point of the optical system for directing the light to said light cable receptacle connector and said optical member.

(8) An ophthalmic laser apparatus according to (7) can have the light cable connected to the probe for photocoagulating an ocular externally of an eye to be treated through a sclera.

(9) An ophthalmic laser apparatus according to (5) can have a semiconductor laser oscillator as the laser oscillator.

BRIEF DESCRIPTION OF THE DRAWINGS

These and other objects and technical advantages of the present invention will be readily apparent from the following description of the preferred exemplary embodiments of the invention in conjunction with the accompanying drawings, in which.

DESCRIPTION OF THE PREFERRED EMBODIMENTS

The embodiments of the present invention are now explained with reference to the drawings.

Embodiment 1

Figure 1:
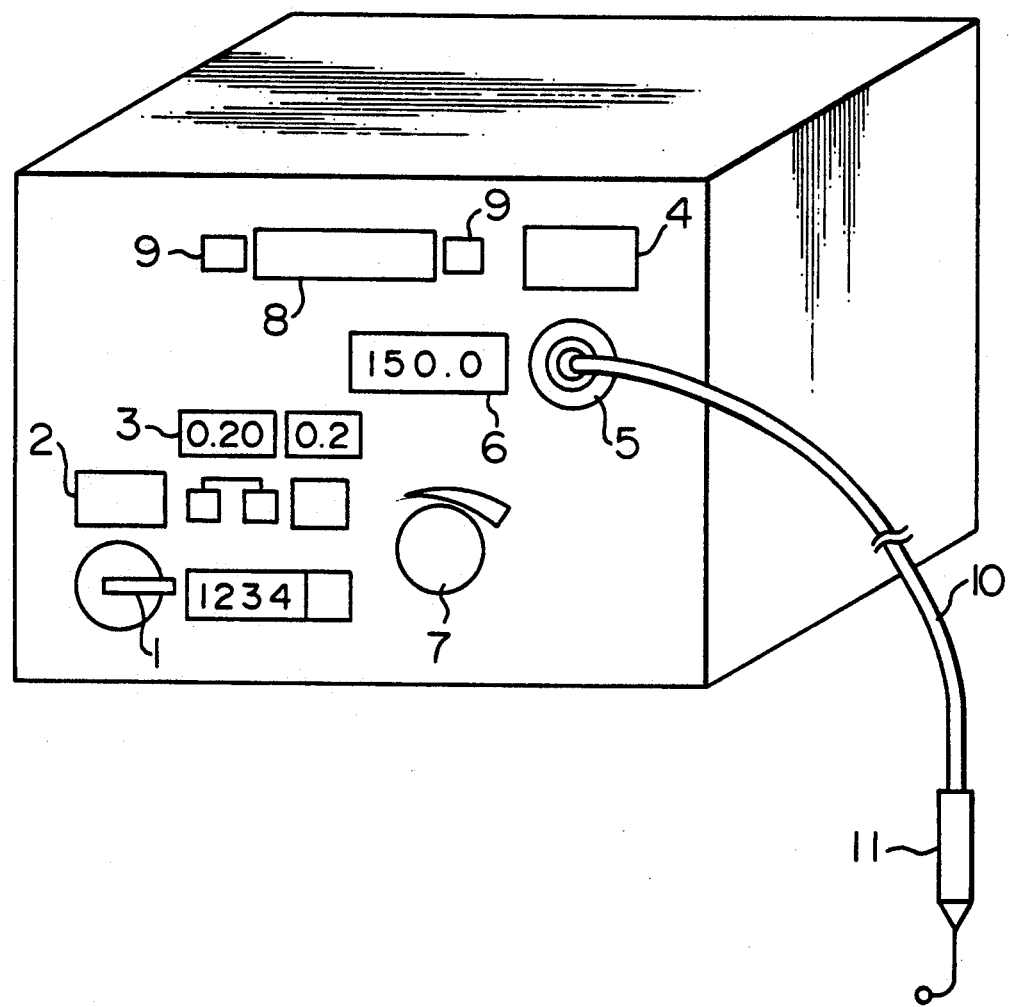
FIG. 1 shows an external perspective view of a body of a semiconductor laser apparatus in one embodiment.

FIG. 1 shows an external perspective view of a body of an ophthalmic laser apparatus of the present embodiment.

Numeral 1 denotes a key switch for turning a power on, and numeral 2 denotes a coagulation switch which is a safety device. When the coagulation switch 2 is turned on, a coagulation light (semiconductor laser beam) is ready to irradiate by a trigger switch. Numeral 3 denotes a coagulation time display and numeral 4 denotes a laser emission indicator to indicate the supply of power to a laser. The laser emission indicator 4 flashes during a waiting time from the turn-on of the key switch 1 to an initial state of the apparatus and when an error occurs in the apparatus. Numeral 5 denotes a fiber connector to which a light cable for directing the coagulation light to delivery optical systems and an end-probe is inserted. Numeral 6 denotes a coagulation output display, numeral 7 denotes a coagulation output knob for setting a coagulation output, numeral 8 denotes an aiming display to indicate a brightness of an aiming light, numeral 9 denotes an aiming switch for controlling a brightness of the aiming light. The above-mentioned apparatus is known as DC-1000, provided by Nidek K. K., which is available on sale in Japan.

Numeral 10 denotes a light cable connected to the fiber connector 5. A transscleral coagulation probe 11 is arranged at one end of the light cable 10. (In the present embodiment, the light cable 10, the probe 11 and a connecting part 30 to be described later are collectively referred to as a probe unit.)

Figure 2:
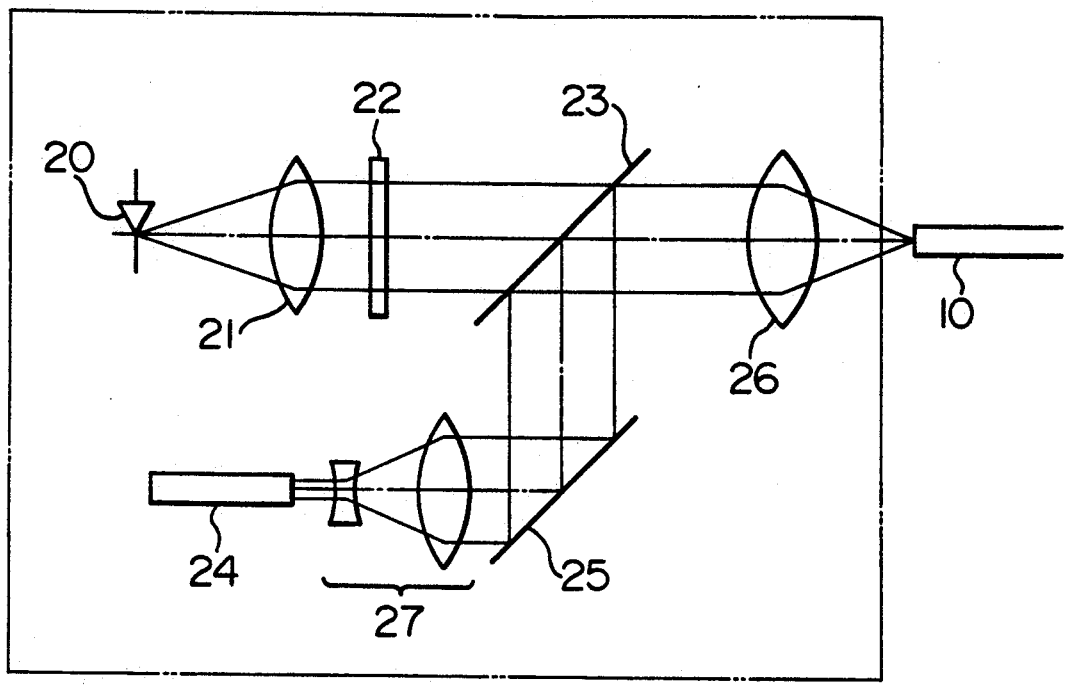
FIG. 2 shows a light directing optical system of an ophthalmic laser apparatus.

A light directing optical system as shown in FIG. 2 is arranged in the ophthalmic laser apparatus.

A beam (approximately 800 nm) emitted from a semiconductor laser 20 which is a coagulation light source arranged in the apparatus is collimated by a collimating lens 21 and a cylindrical lens 22 and it is directed to a dichroic mirror 23, which has a property of transmitting a light of around 800 nm of the semiconductor laser beam and reflecting a He-Ne laser beam which is a visible light. Numeral 24 denotes the He-Ne laser which is an aiming light source. The aiming light emitted from the He-Ne laser 24 is expanded by an expander 27, reflected by a mirror 25, made coaxial with the semiconductor laser beam by the dichroic mirror 23, and focused to a predetermined point by a focusing lens 26.

The focused light beam is directed to an optical fiber in the light cable connected to the fiber connector 5.

Figure 3:
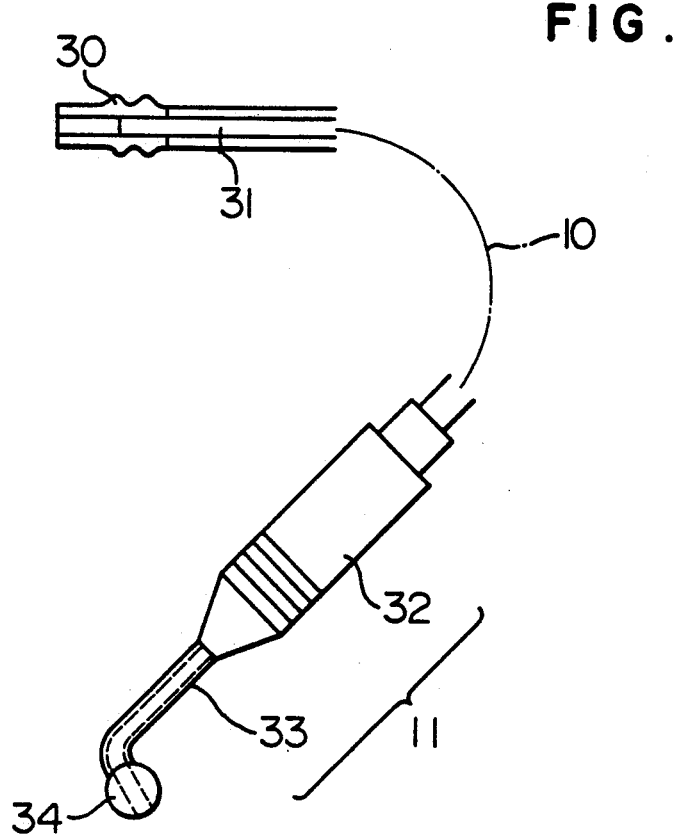
FIG. 3 shows an enlarged view of a transscleral coagulation probe.

FIG. 3 shows an enlarged view of the transscleral coagulation probe unit (including a partial interior view). The probe unit has a connecting part 30 (a positioning pin thereof is omitted because it is well known) which is to be inserted into the fiber connector 5. An end plane of the optical fiber 31 is positioned in the connecting part 30 at the focus point of the focusing lens 24. The optical fiber 31 extends through the light cable 10 and the probe 11 and emits the light from the end of the probe 11. The probe 11 comprises a grip 32 to be held by an operator and a tip 33. An end portion of the tip 33 is bent at approximately 70-90 degrees so that the ocular may be readily pressed with a small cut, that is, by taking the operability for pressing, the limit of loop and the length of the curved portion into consideration. The end thereof is formed with a sphere 34 having a diameter of 2-4 mm so that the pressed portion can be clearly observed through a pupil and the sclera is not damaged. The sphere 34 has a hole to which the tip 33 is fitted and they are bonded together.

While the end of the tip is a spherical in the present embodiment, it may be oval.

A method of treatment by using the present probe is now explained.

The key switch 1 is manipulated to turn on the aiming light. Thus, the coagulation light is ready to be emitted when a foot switch (not shown) is actuated. The end-probe 11 is inserted through a conjunction near the cut eyeball and the end of the tip 33 is pressed to the sclera. The operator observes a deformed portion of the retina and the aiming light transmitted through the sclera and the retina by the binocular indirect ophthalmoscope to bring the aiming light to the portion to be treated. Then, the operator actuates the foot switch (not shown) to irradiate the laser beam to the portion to be treated.

Embodiment 2

In the second embodiment, the connecting part 30 of the probe unit is improved to increase the divergence angle (exit NA) of the light beam at the end of the endprobe.

Figure 4A:
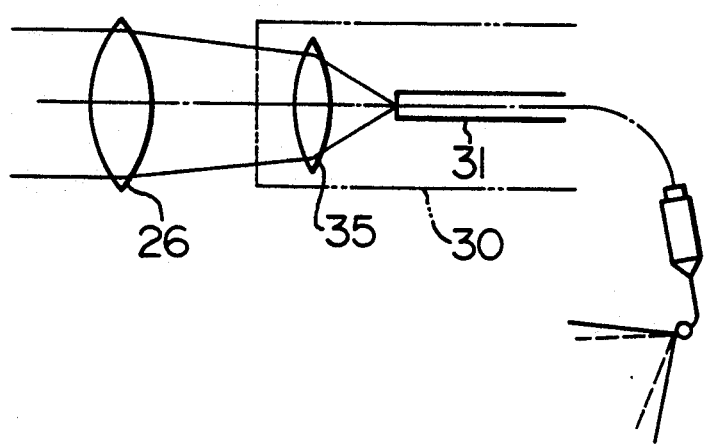
FIGS. 4a and 4b show an improvement of a connecting part 30 of the probe to allow increase and decrease of a divergence angle (exit NA) of a light beam at an end of the probe.

In the embodiment 1, the connecting part 30 which is to be inserted into the fiber connector 5 is constructed such that the end plane of the optical fiber 31 is positioned at the focus point of the focusing lens 26. In the second embodiment, a convex lens 35 (or spherical lens) is provided between the focusing lens 26 and the optical fiber 31 as shown in FIG. 4(a) and the end plane of the optical fiber 31 is positioned at the combined focus point of the convex lens 35 and the focusing lens 26 to vary an incident NA of the light beam from that of the embodiment 1. Since the transscleral retinal coagulation by the semiconductor laser beam is smaller in the coagulation range than that of the cryocoagulation, the concave lens or the spherical lens is arranged at the connecting part 30 to increase the exit NA.

Figure 4B:
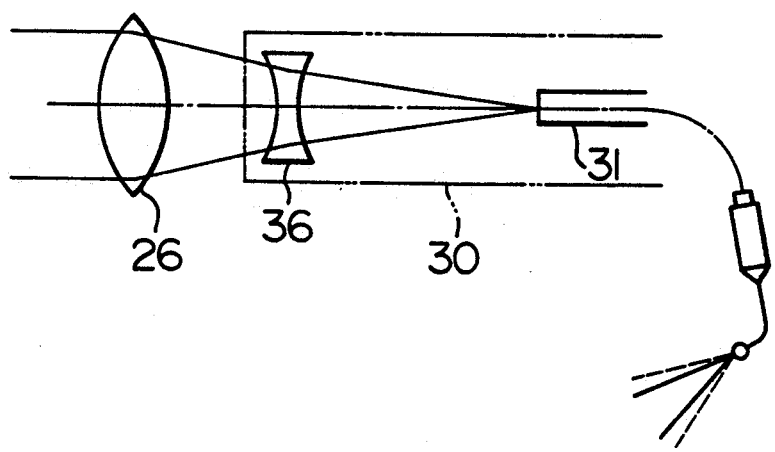
Figure 5A:
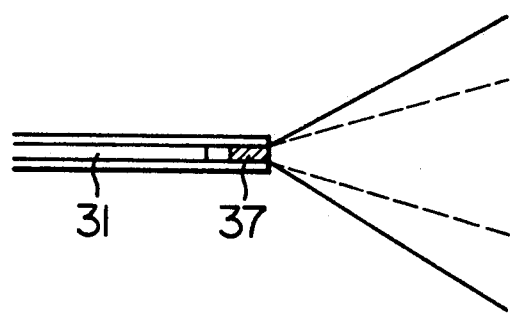
FIGS. 5a–d show an improvement of a tip of the probe to allow increase or decrease of the divergence angle of the light beam at the end of the probe.
Figure 5B:
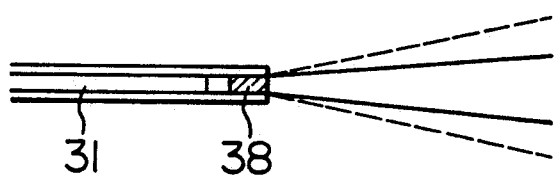
Figure 5C:
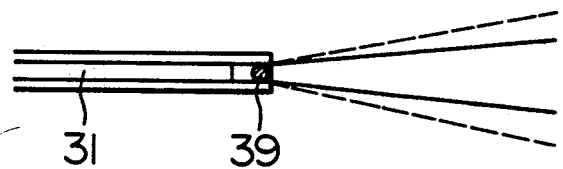
Figure 5D:
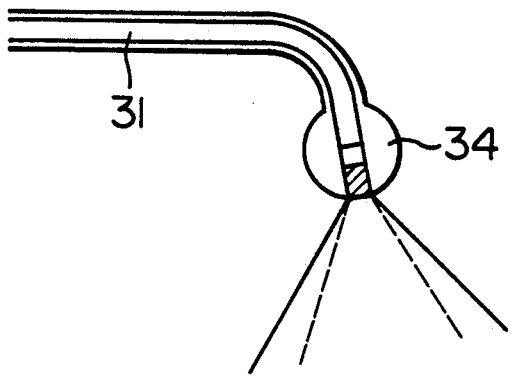

Since it is not possible to converge the semiconductor laser beam beyond a predetermined NA, the optical fiber for delivering the slit lamp preferably has a core diameter of 200 μm (NA 0.1). When an optical fiber having a core diameter of 400 μm is used for the end-probe which is to be inserted into the eye (an inexpensive optical fiber having the core diameter of 400 μm is usually used because the probe unit is disposable, the exit NA of the semiconductor laser beam is larger than that of a conventional Ar laser and the end of the tip must be brought closer to the ocular. As shown in FIG. 4(b), a concave lens 36 is arranged at the connecting part to reduce the exit NA.

Embodiment 3

In the third embodiment, concave and convex distributed index lenses 37 and 38 or a spherical lens 39 are arranged at the tip of the probe to increase or decrease the divergence angle of the light beam at the end of the probe, as is done in the embodiment 2.

A probe having an end diameter of approximately 20 G (0.9 mm) is usually used for the ophthalmic purpose, and the distributed index lens such as SELFOC lens (Trade name of Nippon Sheetglass Corp.) and the ball lens having the diameter of 0.3 mm are presently put to practical use. The divergence angle can be varied in a manner shown in FIGS. 5(a)-5(d). The divergence angle may be controlled by the length of the distributed index lens and the exit NA at the end of the probe may be controlled by the diameter of the spherical lens or by forming it semispherical.

The above embodiments may be modified in various ways and those variations are also covered by the present invention without departing from the technical concept of the present invention.

In accordance with the present invention, the treatment may be safely operated without damaging the sclera even if the probe is inserted externally of the eye to be treated for the photocoagulation treatment.

Further, since the divergence angle of the light beam at the end of the probe is optimized, rapid and safe laser treatment is attained.

While the present invention has been described in detail, it should be understood that various changes, substitutions and alternations can be made thereto without departing from the spirit and scope of the present invention as defined by the appended claims.

What is claimed is:

1. An ophthalmic laser apparatus for generating and directing a laser beam for performing ocular procedures, said apparatus comprising:

laser oscillator means for creating laser light;
   connecting means coupled to said laser oscillator means for transmitting said laser light from the apparatus;
   light cable means having a light cable receptacle connector at one end thereof, said light cable receptacle connector for connecting to said connecting means, and transmitting said laser light therethrough; and
   probe means coupled to a distal end of the light cable means for manipulating the laser light,
   wherein said connecting means comprises an optical member for controlling an exit divergence angle of said laser beam.

2. An ophthalmic laser apparatus according to claim 1 wherein said optical member for controlling the exit divergence angle is a convergence lens.

3. An ophthalmic laser apparatus according to claim 1 wherein said optical member for adjusting the exit divergence angle is arranged at the connecting part of said light cable, and the end plane of the optical fiber in said light cable is positioned at a combined focus point of the optical system for directing the light to said light cable receptacle connector and said optical member.

4. An ophthalmic laser apparatus according to claim 3 wherein said light cable is connected to the probe for transscleral photocoagulation.

5. An ophthalmic laser apparatus according to claim 1 wherein said laser oscillator is a semiconductor laser oscillator.

6. An ophthalmic laser apparatus according to claim 1 wherein said optical member for controlling the exit divergence angle is a divergent lens.

7. A probe unit to be connected to a light source, said light source having a laser oscillator, a receptacle connector and an optical system for directing a laser beam from said laser oscillator to said receptacle connector, said probe unit comprising:

a connecting part to be connected to said receptacle connector;
   a probe member having a bent portion near a distal end thereof, and a spherical portion at the distal end thereof;
   a light cable for connecting said connector and said probe member; and
   means for controlling an incident angle of the laser beam directed from said optical system to control a divergence angle of the laser beam emitted from said probe is provided at said connecting part.

8. A probe unit according to claim 7, wherein means for controlling the divergence angle of the laser beam emitted from said probe is provided in said probe.

9. A probe unit to be connected to a light source, said light source having a laser oscillator, a receptacle connector and an optical system for directing a laser beam from said laser oscillator to said connector, said connector being adapted to be connected with one of various apparatus for directing the laser beam to a part to be treated, said optical system directing said laser beam to said apparatus with a predetermined incident divergence angle, said probe unit comprising:

a connecting part to be connected to said connector;
   a probe;
   a light cable for connecting said connecting part and said probe; and
   controlling means for controlling an exit divergence angle of said laser beam, said controlling means being arranged in said connecting part.

* * * * *